United States Patent [19]

Nakazono et al.

[11] Patent Number: 4,687,863

[45] Date of Patent: Aug. 18, 1987

[54] OPTICALLY ACTIVE HYDROXYIODOLACTONE

[75] Inventors: Yutaka Nakazono, Osaka; Kenji Mori, Tokyo, both of Japan

[73] Assignee: Nitto Electric Industrial Co., Ltd., Osaka, Japan

[21] Appl. No.: 871,217

[22] Filed: Jun. 5, 1986

[30] Foreign Application Priority Data

Dec. 10, 1985 [JP] Japan .................................. 60-278824

[51] Int. Cl.$^4$ ........................................... C07D 307/83
[52] U.S. Cl. .................................................... 549/302
[58] Field of Search .......................................... 549/302

[56] References Cited

PUBLICATIONS

Lythgoe et al., J. C. S. Perkin, I. p. 387–395.

Primary Examiner—Jane T. Fan

Attorney, Agent, or Firm—Sughrue, Mion, Zinn, Macpeak and Seas

[57] ABSTRACT

An optically active hydroxyiodolactone of the formula

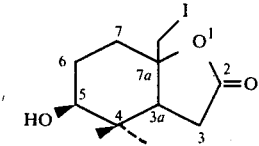

wherein the stereochemistry of the 3a-, 5- and 7a-positions is either (3aR,5S,7aS) or (3aS,5S,7aR). The compound is useful as an intermediate for the production of a large amount of one component of the queen recognizing pheromone of red imported fire ant with a high optical purity.

3 Claims, 4 Drawing Figures

OPTICALLY ACTIVE HYDROXYIODOLACTONE

FIELD OF THE INVENTION

This invention relates to a novel optically active hydroxyiodolactone. More specifically, it relates to a novel optically active hydroxyiodolactone which is useful as an intermediate for the production of a large amount of one component of a queen recognizing pheromone of red imported fire ant (*Solenopsis invicta* Buren) with a high optical purity.

BACKGROUND OF THE INVENTION

Some methods have already been known for the synthesis of dihydroacetinidiolide which is one component of the queen recognizing pheromone of red imported fire ant (*Solenopsis invicta* Buren). One of them starts from a methyl ester of (−)-azafrin which is a carotenoid (W. Eschenmoser, P. Uebelhart and C. H. Engster, *Helv. Chim. Acta.*, 65, 353 (1982)). The starting material of this method is a naturally occurring substance and is not readily available. Furthermore, only the (−)-isomer can be obtained with a low optical purity.

Another known method starts from (4R,6R)-4-hydroxy-2,2,6-trimethylcyclohexanone obtained via asymmetric reduction of 2,2,6-trimethyl-2-cyclohexane-1,4-dione by the action of a yeast (F. Kienzle, H. Meyer, R. E. Minder and H. Thommen, *Helv. Chim. Acta.*, 61, 2616 (1978)). This method, however, can only be applied to the synthesis of an enantiomorph of the (−)-isomer.

SUMMARY OF THE INVENTION

The present inventors have made extensive investigations to overcome the above problems in the synthesis of the above sex pheromone. As a result, it has been found that the use of a novel optically active hydroxyiodolactone in accordance with this invention permits synthesis of large amount of enantiomorphs of the pheromone with a high optical purity.

Accordingly, an object of this invention is to provide a novel optically active hydroxyiodolactone represented by the following structural formula

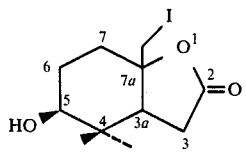

wherein the stereochemistry of the 3a-, 5- and 7a-positions is either (3aR,5S,7aS) or (3aS,5S,7aR).

BRIEF DESCRIPTION OF THE ACCOMPANYING DRAWINGS

DETAILED DESCRIPTION OF THE INVENTION

Figure 1:
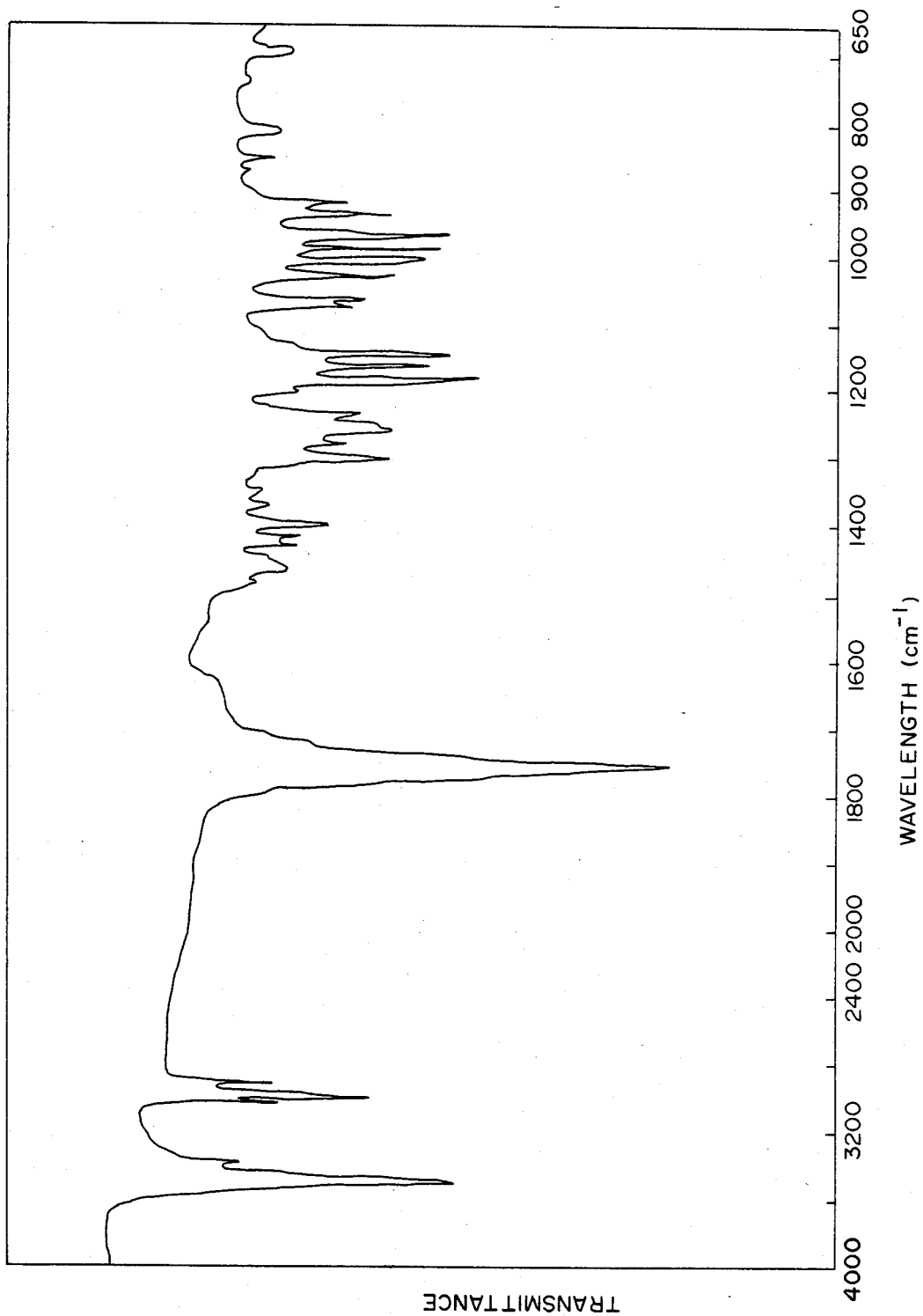
FIG. 1 is an infrared absorption spectrum of (3aS,5S,7aR)-4,4-dimethyl-5-hydroxy-7a-iodomethyl-2-oxooctahydrobenzofuran which is the novel optically active hydroxyiodolactone of this invention represented by formula (2) below.

As is apparent from the structural formula given hereinabove, the optically active hydroxyiodolactone of this invention is specifically (3aR,5S,7aS)-4,4-dimethyl-5-hydroxy-7a-iodomethyl-2-oxooctahydrobenzofuran represented by the following formula (1)

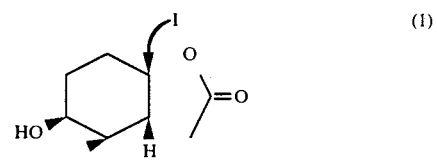

or (3aS,5S,7aR)-4,4-dimethyl-5-hydroxy-7a-iodomethyl-2-oxooctahydrobenzofuran represented by the following formula (2)

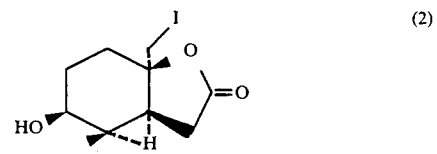

The optically active hydroxyiodolactones (1) and (2) of this invention can be synthesized from known (3S)-2,2-dimethyl-3-hydroxycyclohexanone of the following formula (3)

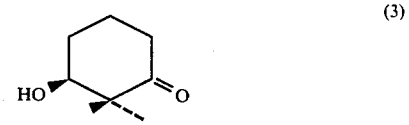

as a starting material (Y. Lu, G. Barth, K. Kieslich, P. D. Strong, W. L. Duax and C. Djerassi, *J. Org. Chem.*, 48, 4549 (1983)).

The process of synthesizing the compound of formula (1) is shown by the following Scheme I.

Scheme I

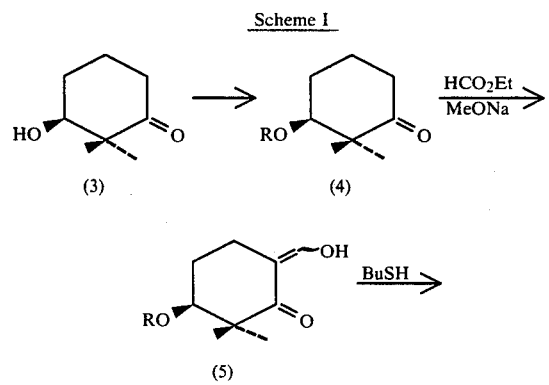

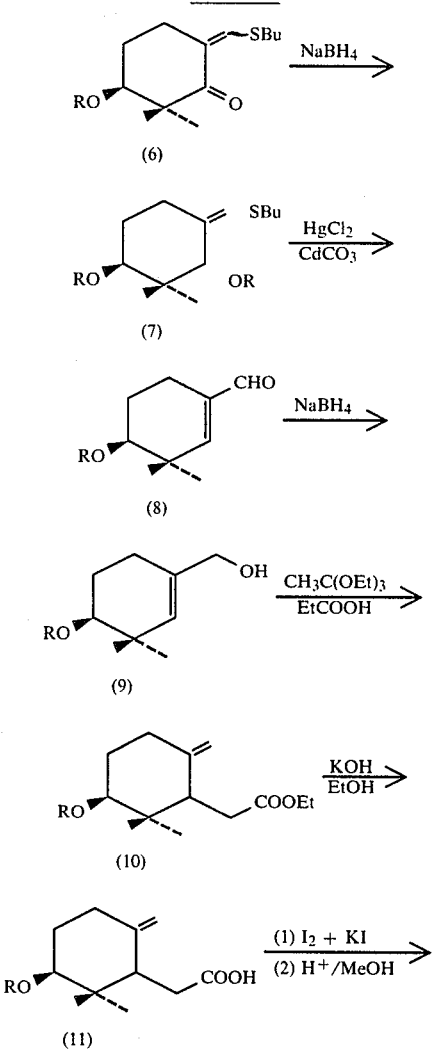

-continued
Scheme I (6), (7), (8), (9), (10), (11)

The individual steps of the process in Scheme I will be described below in detail.

First, the hydroxy group of the hydroxyketone (3) is protected to obtain a compound (4). The protective group R is not particularly limited so long as it is stable under basic conditions. Examples of the protective group include tetrahydropyranyl, methoxymethyl, ethoxymethyl, t-butyldimethylsilyl and benzyl groups. The tetrahydropyranyl group is preferred in view of the stability of the protective group in subsequent reactions, the ease of splitting it off and economy.

Introduction of the protection group into the compound (3) can be carried out in a conventional manner. For example, in the case of introducing the tetrahydropyranyl group, the compound (3) is reacted with 1 to 2 times mole of 2,3-dihydropyrane in dry dichloromethane in the presence of a catalytic amount of p-toluenesulfonic acid. This method is described, for example, in T. W. Green, *Protective Groups in Organic Synthesis*, John Wiley and Sons, New York (1981).

Then, the ketone compound (4) having the protected hydroxyl group is formylated with ethyl formate in the presence of a strong base such as sodium methoxide or lithium diisopropyl amide to give a hydroxyvinyl compound (5). The formylation is well known, and is carried out usually by preparing sodium methoxide (1 to 1.5 times mole of the ketone compound (4)) in an alcoholic solvent such as dry methanol or dry ethanol, adding dry benzene to it, adding a dry tetrahydrofuran solutin of the ketone compound (4) at a temperature of from −10° C. to room temperature, and then adding ethyl formate to the solution in an amount 1 to 2 times mole of the ketone compound (4) usually as a temperature of from 0° C. to room temperature to thereby give the hydroxyvinyl compound (5).

The hydroxyvinyl compound (5) so obtained is then converted to a butylthiomethylene compound (6). This is usually carried out by reacting the hydroxyvinyl compound (5) with 1 to 1.5 times mole of butanethiol in dry benzene in the presence of a catalytic amount of p-toluenesulfonic acid (M. Shiozaki, K. Mori and M. Matsui, *Agric. Biol. Chem.*, 36, 2539 (1972)).

The butylthiomethylene compound (6) is then reduced with sodium borohydride to form an alcohol compound (7). This is accomplished in a conventional manner by, for example, reacting the butylthiomethylene compound (6) with 0.5 to 5 times its equivalent weight of sodium borohydride in ethanol.

The alcohol compound (7) is converted to an α,β-unsaturated aldehyde (8) by, for example, utilizing a method involving the use of mercury (II) chloride. Specifically, the alcohol compound (7) can be converted to the α,β-unsaturated aldehyde compound (8) by heating the alcohol compound (7) under reflux together with an ethanol solution containing 1 equivalent of cadmium carbonate and 1 equivalent of mercury (II) choloride for 1 to 5 minutes (H. J. Bestmann and J. Angerer, *Tetrahedron Letters*, 3665 (1969)).

Then, the α,β-unsaturated aldehyde is converted to an allyl alcohol compound (9) in a conventional manner by, for example, reacting the α,β-unsaturated aldehyde (8) with 0.5 to 5 times its equivalent weight of sodium borohydride in ethanol.

The allyl alcohol compound (9) so obtained is then converted to an exo-allyl alcohol compound (10) by ortho-ester Claisen rearrangement. This reaction can be carried out by dissolving the allyl alcohol compound (9) in 5 to 10 times its equivalent weight of ethyl ortho-acetate, and heating the solution with stirring at a temperature in the range of 120° to 140° C. for several hours in the presence of propionic acid as a catalyst. Preferably, ethanol formed during the reaction is distilled off as the reaction proceeds.

In the next step, the exo-methylene ester compound (10) is hydrolyzed to form an exo-methylene carboxylic acid compound (11). This hydrolysis can be carried out in a conventional manner by, for example, reacting the exo-methylene ester compound (10) in 95% ethanol in the presence of potassium hydroxide at a temperature ranging from room temperature to the boiling point of the solvent for 1 to 5 hours.

The exo-methylenecarboxylic acid compound (11) is converted to an iodolactone compound, and the protective group is split off. Chromatography on a silica gel column gives the compounds of formulae (1) and (2) in accordance with this invention.

The reaction of converting the compound (11) into an iodolactone can be carried out, as is well known, by dissolving the exo-methylenecarboxylic acid compound (11) in ether, adding an aqueous solution containing 1 to 5 times its equivalent weight of sodium hydrogen-carbonate, and adding an aqueous solution containing 1 to 3 times its equivalent weight of iodine and excess potassium iodide at a temperature ranging from room temperature to the boiling point of the solvent. The protective group of the resulting iodolactone compound is then split off. For example, in the case of splitting off the tetrahydropyranyl group, the deprotection may be carried out in accordance with the description of the above-cited Green et al. publication by dissolving the iodolactone in an aqueous solution containing a suitable organic solvent, for example, a hydrocarbon such as benzene, toluene, hexane or cyclohexane, an ether such as diethyl ether or dioxane, or an alcohol such as methanol or ethanol, and then splitting off the tetrahydropyranyl group using an acid. There is no particular restriction on the acid to be used. Examples of suitable acids for this purpose are such inorganic acids as hydrochloric acid, sulfuric acid and phosphoric acid and such organic acids as acetic acid, p-toluenesulfonic acid and methanesulfonic acid. The amount of the acid used is neither restricted, and may range from the catalytic amount to a large excess. The reaction temperature is usually from room temperature to the boiling point of the solvent used.

The hydroxyiodolactone obtained by deprotection is a mixture of the compounds (1) and (2) in accordance with this invention. The mixture can be easily separated into the individual optically active compounds (1) and (2) by, for example, silica gel chromatography.

The optically active hydroxyiodolactones (1) and (2) of this invention obtained as above have an optical purity of as high as 100% ee. These compounds can be converted to the enantiomorphs as one component of the queen recognizing pheromone of red imported fire ant. Specifically, from the compound (1) as a starting material, (S)-(+)-dihydroactinidiolide can be obtained, and from the compound (2) as a starting material, (R)-(−)-dihydroactinidiolide can be obtained.

The process of synthesizing (S)-(+)-dihydroactinidiolide from the compound (1) will now be described by reference to Scheme II.

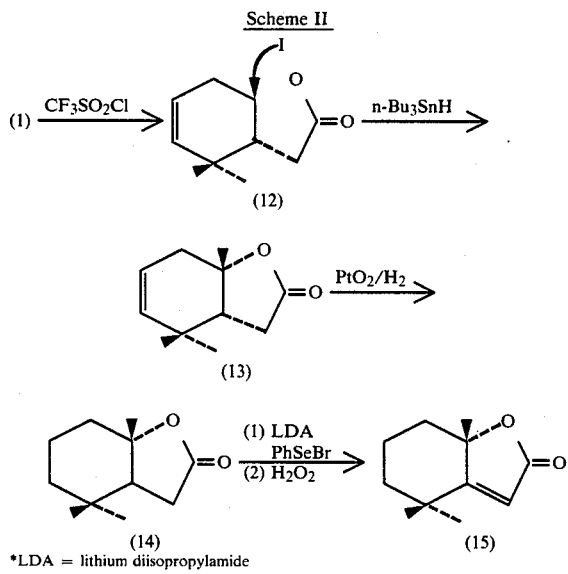

Scheme II

(14)
(15)
*LDA = lithium diisopropylamide

First, dehydration of the compound (1) gives a compound (12). The compound (12) is then deiodinated to form a compound (13). The double bond of the compound (13) is then reduced to form a compound (14). The compound (14) is subjected to phenylselenylation-oxidative splitting to introduce a double bond into the lactone ring to obtain (S)-(+)-dihydroactinidiolide (15).

Evidently, (R)-(−)-dihydroactinidiolide as an enantiomorph of the compound (15) can be obtained by the same reaction process when the compound (2) is used as a starting material.

The optically active hydroxyiodolactones according to this invention are novel compounds. Since, as described above, these compounds can be easily converted to one component of the queen recognizing pheromone of red imported fire ant (*Solenopsis invicta* Burene), they can be suitably used as starting materials for the synthesis of this pheromone in large amounts.

Furthermore, according to the methods described above, the enantiomorphs of the above pheromone can be simultaneously obtained from these starting materials. Separation of the enantiomorphs can give pheromones having an optical purity of 100% ee.

The following examples illustrate the present invention more specifically.

EXAMPLE (a) Synthesis of (3S)-2,2-dimethyl-3-tetrahydropyranyloxycyclohexanone (4)

(3S)-2,2-dimethyl-3-hydroxycyclohexanone (3) (5.12 g, 36.0 mmoles) and dihydropyran (5.00 g., 59.0 mmoles) were dissolved in dry methylene dichloride (90 ml). The solution was cooled in an ice bath, and p-toluenesulfonic acid (50 mg) was added. The resulting mixture was stirred at room temperature for 2 hours. After the reaction, a saturated aqueous solution of sodium hydrogencarbonate was washed with an aqueous solution of sodium chloride and dried over magnesium sulfate. The product was filtered, concentrated, and purified by distillation. Amount yielded 8.14 g (yield 99.9%).

Boiling point: 75°–76° C./0.06 mm Hg

IR (cm$^{-1}$): 2950 (s), 2880 (s), 1710 (s), 1120 (s), 1030 (s), 980 (s).

NMR ($\delta$, CDCl$_3$): 1.12, 1.15, 1.19 and 1.22 (all s, 6H), 1.35–2.60 (m, 12H), 3.20–4.20 (m, 3H), 4.50–4.90 (m, 1H).

(b) Synthesis of (3S)-6-butylthiomethylene-2,2-dimethyl-3-tetrahydropyranyloxycyclohexanone (6)

A flask was charged with 300 ml of a methanol solution containing sodium methoxide (6.95 g, 36.1 mmoles) in a concentration of 28% by weight, and methanol was evaporated under reduced pressure. The inside of the flask was purged with argon, and dry benzene (185 ml) was added. The mixture was cooled over an ice bath. A dry tetrahydrofuran solution (70 ml) of (3S)-2,2-dimethyl-3-tetrahydropyranyloxycyclohexanone (4) (8.14 g, 36.0 mmoles) was added. Then, distilled ethyl formate (3.20 g, 43.2 mmoles) was added, and the mixture are stirred at room temperature for 18 hours.

After the reaction, water (80 ml) was added, and the mixture was further stirred for 15 minutes. The aqueous layer was separated, and the organic layer was extracted three times with a 4% aqueous solution of sodium hydroxide. The extracts were combined with the aqueous layer. The mixture was adjusted to pH 3–4 with concentrated hydrochloric acid, extracted three times with ethyl acetate, and dried over magnesium sulfate The product was filtered and concentrated to give a crude component (5).

The organic layer separated in the first place was concentrated to recover the starting compound (4). The amount of the recovered compound (4) in the unpurified state was 2.00 g (the recovery ratio 25%).

The crude compound (5) was mixed with a small amount of p-toluenesulfonic acid and n-butanethiol (5 ml, 46.7 mmoles) in dry benzene (120 ml), and the mixture was stirred for 4 hours under reflux. The reaction mixture was diluted with diethyl ether, washed with water and then with a saturated aqueous solution of sodium hydrogencarbonate and an aqueous solution of sodium chloride, and dried over magnesium sulfate. The product was filtered and concentrated, and the residue was purified by column chromatography (200 g of silica gel; n-hexane/ethyl acetate) to give 2.08 g of the compound (6). At the same time, 3.39 g of a compound corresponding to the compound (6) from which the tetrahydropyranyl group was removed was formed. This compound was tetrahydropyranylated in a conventional manner, and purified by column chromatography (200 g of silica gel, n-hexane/ethyl acetate). Finally, 6.08 g of the compound (6) was obtained.

IR (cm$^{-1}$): 2950 (s), 2870 (s), 1660 (s), 1540 (s), 1160 (s), 1030 (s).

NMR ($\delta$, CDCl$_3$): 0.70–3.05 (m, 25H), 3.73 (m, 3H), 4.75 (m, 1H), 7.58 (m, 1H).

(c) Synthesis of (3S)-6-butylthiomethylene-2,2-dimethyl-3-tetrahydropyranyloxycyclohexan-1-ol (7)

The compound (6) obtained above, i.e., (3S)-6-butylthiomethylene-2,2-dimethyl-3-tetrahydropyranyloxycyclohexanone, (2.08 g, 6.4 mmoles) was dissolved in tetrahydrofuran (25 ml), and the solution was cooled over an ice bath. To the solution was added dropwise a 95% ethanol solution (30 ml) of sodium borohydride (0.61 g, 16 mmoles) so that the temperature did not rise above 6° C. After the addition, the mixture was stirred for 2 hours at a temperature not exceeding 10° C. Most of the solvent was evaporated under reduced pressure. Water was added to the residue, and the mixture was extracted with ether. The ethereal layer was washed with an aqueous solution of sodium chloride, dried over magnesium sulfate, filtered, dried, and concentrated to give 2.00 g of a crude alcohol compound (7).

IR (cm$^{-1}$): 3450 (s), 2950 (s), 2875 (s), 1455 (s), 1435 (m), 1020 (s).

(d) Synthesis of (4S)-3,3-dimethyl-4-tetrahydropyranyloxycyclohexene-1-carbaldehyde (8)

The crude compound (7) (2.00 g), cadmium carbonate (1.10 g, 6.4 mmoles) and mercury dichloride (1.74 g, 6.4 mmoles) were added to 95% ethanol (45 ml), and the solution was stirred for 5 minutes under reflux. After cooling, benzene and water were added, and the mixture was filtered through Celite. The filtrate was extracted twice with benzene, washed with an aqueous solution of sodium chloride, and dried over magnesium sulfate. The product was filtered and concentrated to give 1.32 g of a crude compound (8). At the same time, a compound corresponding to the compound (8) from which the tetrahydropyranyl group was removed formed as a by-product. This by-product was tetrahydropyranylated in a conventional manner, and purified by column chromatography (50 g of silica gel; n-hexane/ethyl acetate). Finally, the compound (8) was obtained in an amount of 0.71 g (in a yield of 47% from the compound (6)).

IR (cm$^{-1}$): 2950 (s), 2870 (s), 2700 (w), 1685 (s), 1640 (s), 1030 (s).

NMR ($\delta$, CDCl$_3$): 1.08, 1.10 and 1.28 (all s, 6H), 1.35–2.45 (m, 10H), 3.15–4.10 (m, 3H), 4.70 (m, 1H), 6.35 (m, 1H), 9.50 (s, 1H).

(e) Synthesis of (4S)-3,3-dimethyl-4-tetrahydropyranyloxy-1-hydroxymethylcyclohexene (9)

(4S)-3,3-dimethyl-4-tetrahydropyranyloxycyclohexene-1-carbaldehyde (8) (0.71 g, 2.98 mmoles) was dissolved in tetrahydrofuran (7 ml), and a 95% ethanol solution of sodium borohydride (0.38 g, 10 mmoles) was added dropwise over an ice bath. After the addition, the mixture was stirred for 2 hours at a temperature below 10° C. The solvent was evaporated under reduced pressure. The residue was diluted with water, and extracted twice with diethyl ether. The ethereal layer was dried over magnesium sulfate, filtered, concentrated, and purified by column chromatography (30 g of silica gel; n-hexane/ethyl acetate) to give 0.65 g (yield 91.3%) of a compound (9).

IR (cm$^{-1}$): 3400 (s), 2950 (s), 2875 (s), and 1025 (s).

NMR ($\delta$, CCl$_4$): 0.85–2.30 (m, 16H), 3.15–3.80 (m, 3H), 3.82 (s, 2H), 4.50–4.80 (m, 1H), 5.25 (br s, 1H).

(f) Synthesis of ethyl[(1RS,3S)-2,2-dimethyl-6-methylene-3-tetrahydropyranyloxycyclohexyl]acetate (10)

Compound (9) (9.45 g, 39.3 mmoles) and propionic acid were dissolved in newly distilled ethyl ortho-acetate (51.0 g, 314 mmoles). The solution was stirred at 140° C. for 6 hours while distilling off ethanol. Ethyl ortho-acetate was removed from the resulting reaction mixture, and the residue was concentrated. After cooling, the residue was diluted with ether. The ether solution was washed with a saturated aqueous solution of sodium hydrogencarbonate and then with an aqueous solution of sodium chloride, dried over magnesium sulfate, and concentrated under reduced pressure. The residue was purified by column chromatography (200 g of silica gel; n-hexane/ethyl acetate) to give a compound (10) as a mixture of the (1S,3S)-isomer and (1R,3S)-isomer (11.7 g, 37.7 mmoles, yield 96%).

$n_D^{22}$: 1.4774.

$[\alpha]_D^{22}$: +25.5° (c=0.81, CHCl$_3$).

IR (cm$^{-1}$): 3100 (w), 1740 (s), 1650 (m), 1030 (s), 890 (m).

NMR ($\delta$, CDCl$_3$): 0.73–1.08 (m, 6H), 1.23 (t, 3H, J=7 Hz), 1.36–2.78 (m, 13H), 3.18–4.20 (m, 3H), 4.10 (q, 2H, J=7 Hz), 4.48–4.86 (m, 3H).

Elemental analysis: Found: C, 69.31; H, 9.72. Calcd (for C$_{18}$H$_{30}$O$_4$): C, 69.64; H, 9.74.

As a result of analysis of the corresponding 3-benzoyloxy derivatives of the (1S,3S)-isomer and (1R,3S)-isomer in this mixture by HPLC chromatography (column: Nucleosil (registered trademark) 50-5, n-hexane/tetrahydrofuran/methanol), the mixture was composed of 64% of the (1S,3S)-isomer and 36% of the (1R,3S)-isomer.

(g) Synthesis of (1'RS,3'S)-2',2'-dimethyl-6'-methylene-3'-tetrahydropyranyloxycyclohexylacetic acid (11)

The compound (10) was dissolved in an ethanol solution containing 2.5% of potassium hydroxide, and the solution was heated under reflux for 2 hours. After the reaction, ethanol was distilled off under reduced pressure. Water was added to the residue, and the mixture was acidified to pH 4 with 1N hydrochloric acid, and extracted with ether twice. The ether solution was washed with an aqueous solution of sodium chloride, dried over magnesium sulfate, and concentrated under reduced pressure to give a crude compound (11) (10.6 g).

IR ($cm^{-1}$): 3100 (br s), 1725 (s), 1025 (s).

This crude compound (11) was used in the following reaction without purification.

(h) Synthesis of (3aRS,5S,7aRS)-4,4-dimethyl-7a-iodomethyl-2-oxo-3-tetrahydropyranyloxyoctahydrobenzofuran A 0.5M aqueous solution of sodium hydrogen-carbonate (120 ml) was added to a solution of the compound (11) (10.6 g, 37.7 mmoles) in ether (120 ml), and the mixture was stirred at room temperature for 20 minutes. The mixture was then refluxed, and an aqueous solution (150 ml) containing potassium iodide (37.8 g) and iodine (19.2 g) was gradually added, and the mixture was stirred overnight under reflux. After cooling, the reaction mixture was washed with an aqueous solution of sodium thiosulfate, an aqueous solution of sodium hydrogencarbonate and then an aqueous solution of sodium chloride, dried over magnesium sulfate, and concentrated under reduced pressure to give a crude desired compound (14.5 g, 35.5 mmoles).

IR ($cm^{-1}$): 1780 (s), 1460 (s), 1160 (s), 1030 (s).

NMR ($\delta$, $CDCl_3$): 0.83–1.20 (m, 6H), 1.30–2.45 (m, 11H), 2.60 (s, 2H), 3.21–4.11 (m, 5H), 4.66 (m, 1H).

This compound was used in the following reaction without purification.

(i) Synthesis of (3aR,5S,7aS)-4,4-dimethyl-5-hydroxy-7a-iodomethyl-2-oxooctahydrobenzofuran (1) and its enantiomorph, (3aS,5S,7aR)-isomer (2)

0.5% p-toluenesulfonic acid was dissolved in methanol (150 ml), and (3aRS,5S,7aRS)-4,4-dimethyl-7a-iodomethyl-2-oxo-3-tetrahydropyranyloxyoctahydrobenzofuran obtained in (h) above was dissolved in the solution. The solution was stirred at room temperature for 8 hours. Methanol was evaporated under reduced pressure. The residue was diluted with ethyl acetate. The ethyl acetate solution was washed with a saturated aqueous solution of sodium hydrogencarbonate and then with an aqueous solution of sodium chloride, dried over magnesium sulfate, and concentrated under reduced pressure.

The residue was treated by column chromatography (150 g of silica gel, n-hexane/ethyl acetate (7:3)) to give the compound (2) (3.60 g, 11.1 mmoles, yield 30% from the compound (10)). Recrystallization from n-hexane/ethyl acetate gave the compound (2) in an amount of 3.23 g.

Figure 2:
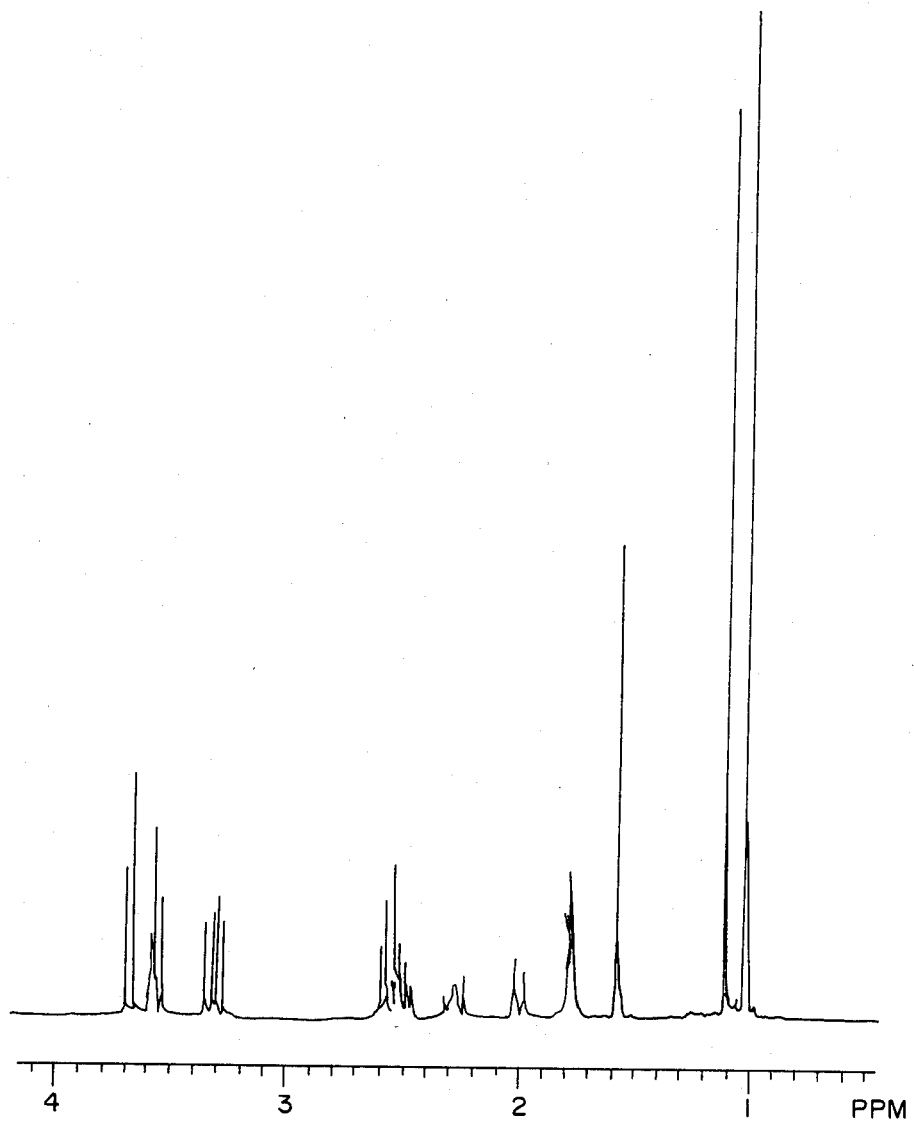
FIG. 2 is a proton nuclear magnetic resonance spectrum (400 MHz) of the compound of formula (2)

The infrared absorption spectrum of the compound (2) is shown in FIG. 1, and its proton NMR spectrum, in FIG. 2.

Melting point: 134.5°–135.0° C.

$[\alpha]_D^{22}$: −11.1° (c=0.075, $CHCl_3$).

IR (KBr, $cm^{-1}$): 3490 (s, sh), 1755 (vs), 1180 (s), 1155 (m), 1140 (s), 1020 (m), 1000 (m), 980 (s), 960 (s).

NMR ($\delta$, 400 MHz, $CDCl_3$): 1.02 (s, 3H), 1.11 (s, 3H, 1.59 (d, 1H, J=3.5 Hz), 1.78 (ddd, 1H, J=3.5 Hz, 4 Hz, 7 Hz), 1.79 (ddd, 1H, J=3.5 Hz, 4 Hz, 10.5 Hz), 2.00 (dddd, 1H, J=1.2 Hz, 4 Hz, 4 Hz, 14.5 Hz), 2.28 (ddd, 1H, J=7 Hz, 10.5 Hz, 14.5 Hz), 2.49 (dd, 1H, J=8.5 Hz, 11 Hz), 2.56 (dd, 1H, J=8.5 Hz, 16.5 Hz), 3.32 (dd, 1H, J=11 Hz, 16.5 Hz), 3.55 (d, 1H, J=11.5 Hz), 3.58 (ddd, 1H, J=3.5 Hz, 3.5 Hz, 3.5 Hz), 3.68 (d, 1H, J=11.5 Hz).

Elemental analysis: Found: C, 40.79; H, 4.99. Calcd (for $C_{11}H_{17}O_3I$): C, 40.75; H, 5.28.

Elution with n-hexane/ethyl acetate (1:1) gave crystalline (3aR,5S,7aS)-compound (1) (600 g, 18.5 mmoles, yield 49% from the compound (10)). Recrystallization from ether gave the compound (1) in an amount of 4.22 g.

Figure 3:
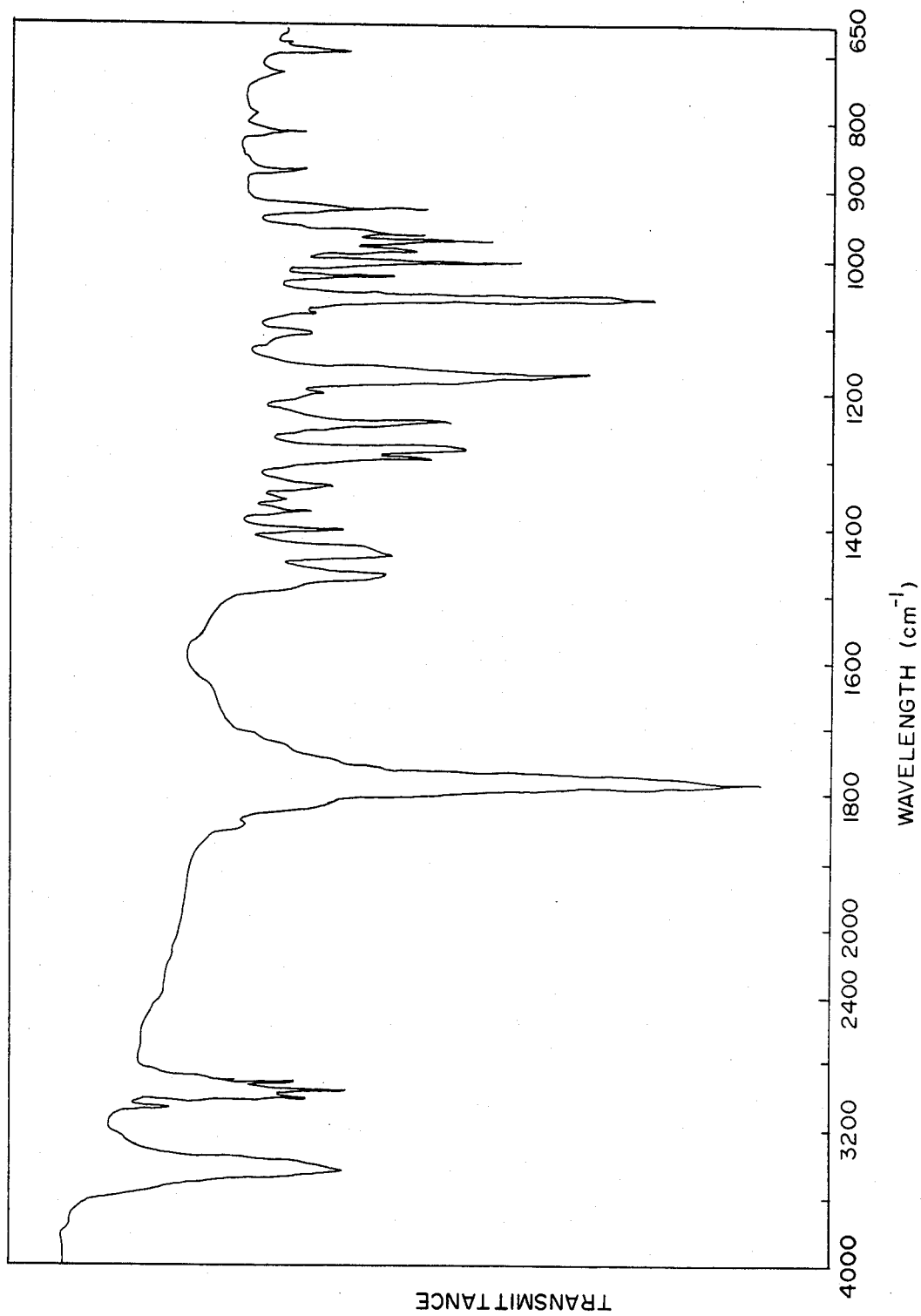
FIG. 3 is an infrared absorption spectrum of (3aR,5S,7aS)-4,4-dimethyl-5-hydroxy-7a-iodomethyl-2-oxooctahydrobenzofuran which is also the novel optically active hydroxyiodolactone of this invention represented by formula (1) below.
Figure 4:
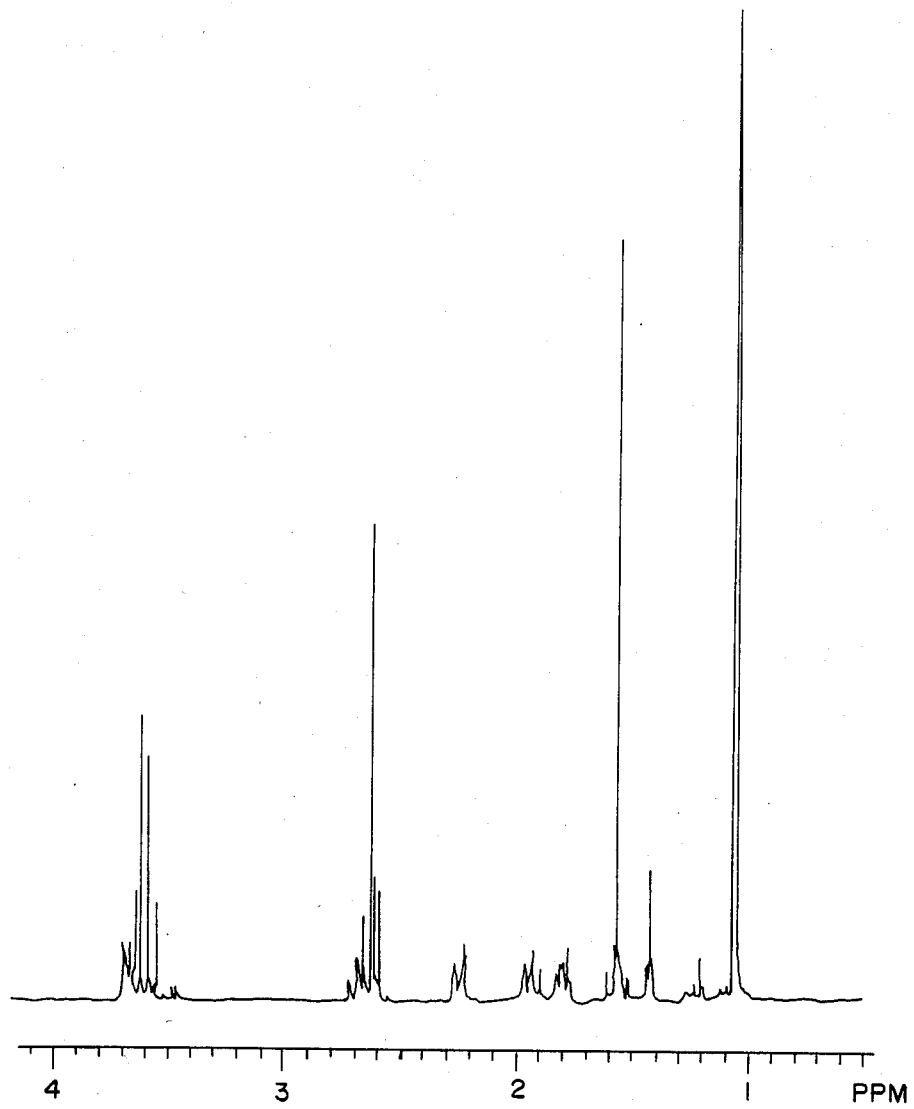
FIG. 4 is a proton nuclear magnetic resonance spectrum (400 MHz) of the compound of formula (1).

The infrared absorption spectrum of the compound (1) is shown in FIG. 3, and its proton NMR spectrum, in FIG. 4.

Melting point: 136.0°–136.5° C.

$[\alpha]_D^{22}$: +35.5° (c=0.095, $CHCl_3$).

IR (KBr, $cm^{-1}$): 3450 (m, br), 1780 (vs, sh), 1165 (s), 1055 (s), 1000 (m), 965 (m).

NMR ($\delta$, 400 MHz, $CDCl_3$): 1.04 (s, 3H), 1.06 (s, 3H), 1.43 (d, 1H, J=4.7 Hz), 1.56 (dddd, 1H, J=4 Hz, 10.5 Hz, 12 Hz, 14 Hz), 1.80 (dddd, 1H, J=4.5 Hz, 4.5 Hz, 4.5 Hz, 14 Hz), 1.93 (ddd, 1H, J=4.5 Hz, 12 Hz, 15 Hz), 2.24 (dddd, 1H, J=2 Hz, 4 Hz, 4.5 Hz, 15 Hz), 2.61 (d, 1H, J=12 Hz), 2.62 (d, 1H, J=7.5 Hz), 2.69 (ddd, 1H, J=2 Hz, 7.5 Hz, 12 Hz), 3.58 (d, 1H, J=11.5 Hz), 3.64 (d, 1H, J=11.5 Hz), 3.68 (ddd, 1H, J=4.5 Hz, 4.7 Hz, 10.5 Hz).

Elemental analysis: Found: C, 40.48; H, 5.11 Calcd (for $C_{11}H_{17}O_3I$): C, 40.75; H, 5.28.

REFERENCE EXAMPLE

(a) Synthesis of (3aR,7aS)-4,4-dimethyl-7a-iodomethyl-2-oxo-2,3,3a,4,7,7a-hexahydrobenzofuran (12), (3aR,4RS,7aS)-7a-iodomethyl-5-methyl-4-methylene-2-oxooctahydrobenzofuran, and (3aR,5R,7aS)-5-chloro-4,4-dimethyl-7a-iodomethyl-2-oxooctahydrobenzofuran Compound (1) (4.00 g, 12.3 mmoles) and 4-(N,N-dimethylamino)pyridine (7.50 g, 61.5 mmoles) were dissolved in dry methylene dichloride (80 ml). To the solution was added dropwise trifluoromethanesulfonyl chloride (4.50 g, 26.7 mmoles) at 5° to 15° C. with stirring in an argon atmosphere. After the addition, the mixture was stirred at 5° C. for 10 minutes, and further at room temperature for 1 hour. Water was added to the reaction mixture, and the mixture was stirred for 30 minutes. The reaction mixture was washed with water and then with an aqueous solution of sodium chloride, dried over magnesium sulfate, and concentrated under reduced pressure. The residue was purified by column chromatography (150 g of silica gel).

The first eluate obtained by elution with n-hexane/ethyl acetate (40:1) gave (3aR,4RS,7aS)-7a-iodomethyl-5-methyl-4-methylene-2-oxooctahydrobenzofuran (0.240 g, yield 6.4%).

$n_D^{23.5}$: 1.5578.

$[\alpha]_D^{23.5}$: +16.0° (c=0.82, $CHCl_3$).

IR ($cm^{-1}$): 3100 (w), 3050 (w), 1780 (s), 1645 (m).

NMR (δ, CDCl$_3$): 1.25 (d, 3H, J=7 Hz), 1.00–3.30 (m, 8H), 3.35 (d, 1H, J=12 Hz), 3.55 (d, 1H, J=12 Hz), 5.00 (br s, 2H).

Elemental analysis: Found: C, 43.42; H, 4.87. Calcd (for C$_{11}$H$_{15}$O$_2$I): C, 43.15; H, 4.94.

The second eluate obtained by elution with n-hexane/ethyl acetate (40:1) gave the compound (12) (2.94 g, yield 78%).

n$_D^{22}$: 1.5542.

[α]$_D^{22}$: +124.8° (c=1.56, CHCl$_3$).

IR (cm$^{-1}$): 3050 (m), 1780 (s), 1660 (w).

NMR (δ, CDCl$_3$): 1.05 (s, 3H), 1.10 (s, 3H), 2.58 (m, 5H), 3.38 (d, 1H, J=12 Hz), 3.68 (d, 1H, J=12 Hz), 5.65 (br s, 2H).

Elemental analysis: Found: C, 43.02; H, 4.94. Calcd (for C$_{11}$H$_{15}$O$_2$I): C, 43.15; H, 4.94.

The third eluate obtained by elution with n-hexane/ethyl acetate (40:1) gave crystalline (3aR,5R,7aS)-5-chloro-4,4-dimethyl-7a-iodomethyl-2-oxooctahydrobenzofuran (0.253 g, yield 6.0%).

Melting point: 127.0°–127.5° C.

[α]$_D^{24}$: −19.2° (c=1.57, CHCl$_3$).

IR (cm$^{-1}$): 3010 (s), 3000 (s), 2960 (s), 2920 (s), 1780 (s).

NMR (δ, 100 MHz, CDCl$_3$): 1.16 (s, 3H), 1.18 (s, 3H), 1.93–3.41 (m, 7H), 3.49 (d, 1H, J=12 Hz), 3.64 (d, 1H, J=12 Hz), 3.99 (dd, 1H, J=4 Hz, 4 Hz).

Elemental analysis: Found: C, 38.50; H, 4.74. Calcd (for C$_{11}$H$_{16}$O$_2$ClI): C, 38.56; H, 4.71.

(b) Synthesis of (3aR,7aS)-2-oxo-4,4,7a-trimethyl-2,3,3a,4,7,7a-hexahydrobenzofuran (13)

Compound (12) (2.90 g, 9.47 mmoles) was dissolved in dry benzene (7.5 ml), and while the solution was stirred with ice cooling, tri-n-butyltin hydride (5.60 g, 19.2 mmoles) was added dropwise to it in an argon atmosphere. The reaction mixture was stirred overnight at room temperature and purified by column chromatography (130 g of silica gel; n-hexane/ethyl acetate) to give compound (13) (1.70 g; yield 99.6%). By distillation, a purified product for analysis was obtained.

Boiling point: 100°–110° C. (bath temperature)/0.2 mm Hg.

n$_D^{23.5}$: 1.4815.

[α]$_D^{23.5}$: +170.0° (c=1.09, CHCl$_3$).

IR (cm$^{-1}$): 3060 (m), 1780 (m), 1660 (w), 1385 (m), 1230 (m), 1180 (m), 1095 (m), 950 (m), 725 (m).

NMR (δ, CDCl$_3$): 1.02 (s, 3H), 1.10 (s, 3H), 1.55 (s, 3H), 2.00–2.85 (m, 5H), 5.60 (m, 2H).

Elemental analysis: Found: C, 73.06; H, 8.92. Calcd (for C$_{11}$H$_{16}$O$_2$): C, 73.30; H, 8.95.

(c) Synthesis for (3aR,7aS)-2-oxo-4,4,7a-trimethyloctahydrobenzofuran (14)

Compound (13) (1.00 g, 5.55 mmoles) was dissolved in dry acetic acid, and platinum oxide (0.10 g) was added to the solution. The mixture was shaken for 23 hours under hydrogen pressure (30 atms.). The catalyst was separated by filtration, and the filtrate was concentrated under vacuum. The residue was diluted with ethyl acetate, and the ethyl acetate solution was washed with an aqueous solution of sodium hydrogen-carbonate, water and an aqueous solution of sodium chloride in this order, dried over magnesium sulfate, and concentrated under vacuum. The residue was purified by column chromatography (10 g of silica gel; n-hexane/ethyl acetate) to give crystalline (3aR,7aS)-isomer (14) (0.910 g, yield 80%). Recrystallization from n-hexane gave 0.669 g of the purified compound (14).

Melting point: 74°–75° C.

[α]$_D^{24}$: +63.5° (c=0.95, CHCl$_3$)

IR (cm$^{-1}$): 1700 (s), 1265 (s), 1100 (s), 945 (s).

NMR (δ, 400 MHz, CDCl$_3$): 0.91 (s, 3H), 1.05 (s, 3H), 1.53 (s, 3H), 1.28–1.65 (m, 5H), 1.86 (br d, 1H, J=12.5 Hz), 2.07 (dd, 1H, J=8.7 Hz, 12.5 Hz), 2.43 (dd, 1H, J=8.7 Hz, 15.4 Hz), 2.51 (dd, 1H, J=12.5 Hz, 15.4 Hz).

Elemental analysis: Found: C, 72.40; H, 9.74. Calcd (for C$_{11}$H$_{18}$O$_2$): C, 72.49; H, 9.95.

(d) Synthesis of (3aR,7aS)-2-oxo-3-phenylselenyl-4,4,7a-trimethyloctahydrobenzofuran Diisopropylamine (0.45 g, 4.4 mmoles) was dissolved in dry tetrahydrofuran (2 ml), and an n-hexane solution (1.52N, 2.2 ml) of n-butyllithium was added to the solution at −70° to −55° C. with stirring in an argon atmosphere to prepare a solution of lithium diisopropylamide. The solution was then stirred at −10° C. for 10 minutes, and then cooled to −70° C.

A solution of the (3aR,7aS)-compound (14) (0.40 g, 2.20 mmoles) in dry tetrahydrofuran (3 ml) was gradually added to the reaction mixture over 1 hour with stirring. The reaction mixture was then stirred at −70° C. for 20 minutes, and hexamethylphosphorous triamide (0.7 ml) was added.

PhSeSePh (2.75 g, 8.8 mmoles) was dissolved in dry tetrahydrofuran (5 ml). Bromine (0.45 ml, 8.8 mmoles) was added rapidly to this solution at room temperature with stirring to prepare a dry tetrahydrofuran solution (3.5 mole/liter, 1.6 ml) of PhSeBr. Thereafter, the reaction temperature was gradually raised to room temperature. 1N hydrochloric acid (5 ml) was added to the reaction mixture, and the mixture was diluted with ether. The ether solution was washed with an aqueous solution of sodium chloride, dried over magnesium sulfate, and concentrated to dryness. The residue was purified by column chromatography (silica gel 20 g; n-hexane/ethyl acetate) to give (3aR,7aS)-2-oxo-3-phenylselenyl-4,4,7a-trimethyloctahydrobenzofuran (0.70 g).

IR (cm$^{-1}$): 3080 (m), 1765 (s), 1580 (m), 1480 (m), 1440 (m), 1380 (m), 1100 (s), 960 (m), 785 (s), 740 (s), 690 (s).

NMR (δ, CDCl$_3$): 1.00 (s, 3H), 1.19 (s, 3H), 1.32 (s, 3H), 0.80–2.40 (m, 6H), 1.92 (d, 1H, J=10 Hz), 3.02 (d, 1H, J=10 Hz), 7.10–7.52 (m, 3H), 7.52–7.80 (m, 2H).

This product was used in the following reaction without purification.

(e) Synthesis of (5)-(+)-oxo-4,4,7a-trimethyl-2,4,5,6,6,7a-hexahydrobenzofuran (15) [(+)-dihydroactinidiolide (15)]

(3aR,7aS)-2-oxo-3-phenylselenyl-4,4,7a-trimethyloctahydrobenzofuran (0.62 g) and acetic acid (one drop) were dissolved in tetrahydrofuran (10 ml), and while the solution was cooled with ice with stirring, a 35% aqueous solution of hydrogen peroxide (0.8 ml, 9.15 mmoles) was added, and the mixture was stirred at 5° C. for 1 hour. A small amount of platinum was added, and the excess of hydrogen peroxide was decomposed. A saturated aqueous solution of sodium hydrogencarbonate was added, and the mixture was stirred at room temperature for 30 minutes. Thereafter, the reaction mixture was diluted with ether. The ether solution was washed with a saturated aqueous solution of sodium hydrogen-carbonate, water and an aqueous solution of sodium chloride in this order, dried over magnesium sulfate, and concentrated to dryness. The residue was purified by column chromatography (20 g of silica gel; n-hexane/ethyl acetate) to give (S)-(+)-compound (15) (0.120 g).

Melting point: 67°–68° C.

$[\alpha]_D^{22}$: +120.9° (c=1.00, CHCl$_3$).

IR (cm$^{-1}$): 3040 (m), 3020 (m), 2980 (s), 2960 (s), 2880 (s), 1750 (s, br), 1635 (s), 1465 (s), 1390 (m), 1375 (s), 1370 (s), 1330 (m), 1300 (w), 1265 (s), 1230 (s), 1195 (s), 1185 (a), 1155 (s), 1125 (s), 1070 (w), 1035 (s), 1015 (w), 995 (s), 985 (s), 960 (s), 950 (s), 915 (s), 885 (s), 860 (s), 790 (w), 703 (s), 685 (s), 660 (w).

NMR (δ, 400 MHz, CDCl$_3$): 1.22 (s, 3H), 1.28 (s, 3H), 1.28 (ddd, 1H, J=5 Hz, 12.5 Hz, 12.5 Hz), 1.46 (ddd, 1H, J=5 Hz, 12.5 Hz), 1.55 (s, 3H), 1.62–1.81 (m, 3H), 2.24 (ddd, 1H, J=2.5 Hz, 5 Hz, 12.5 Hz), 5.65 (s, 1H).

Elemental analysis: Found: C, 73.60; H, 9.01. Calcd (for C$_{11}$H$_{16}$O$_2$): C, 73.30; H, 8.95.

(f) Synthesis of (3aS,7aR)-4-4-dimethyl-7a-iodomethyl-2-oxo-2,3,3a,4,7-,7a-hexahydrobenzofuran (12) [(3aS,7aR-compound (12)]

In the same way as in the preparation of the (3aR,7aS)-compound (12), the (3aS,7aR)-compound (12) (3.54 g, yield 94%) was obtained from the compound (2) (3.99 g).

$n_D^{23}$: 1.5536.

$[\alpha]_D^{23}$: −130.7° (c=1.58, CHCl$_3$).

Elemental analysis: Found: C, 43.09; H, 4.94. Calcd (for C$_{11}$H$_{15}$O$_2$I): C, 43.15; H, 4.94.

The IR and NMR spectra of the (3aS,7aR)-compound (12) were the same as those of the (3aR,7aS)-compound (12).

(g) Synthesis of (3aS,7aR)-2-oxo-4,4,7a-trimethyl-2,3,3a,4,7,7a-hexahydrobenzofuran (13) [(3aS,7aR)-(−)-compound (13)]

In the same way as the preparation of the (3aR,7aS)-compound, (3aS,7aR)-(−)-compound (13) (1.69 g, yield 87%) was obtained from the (3aS,7aR)-compound (12) (3.30 g). By distillation, a purified product of this compound for analysis was prepared.

Boiling point: 100°–105° C. (bath temperature)/0.2 mm Hg.

$n_D^{24}$: 1.4812.

$[\alpha]_D^{24}$: −183.2° (c=1.02, CHCl$_3$).

Elemental analysis: Found: C, 73.12; H, 8.80. Calcd (for C$_{11}$H$_{16}$O$_2$): C, 73.30; H, 8.95.

The IR and NMR spectra of the (3aS,7aR)-compound (13) were the same as those of the (3aR,7aS)-compound (13).

(h) Synthesis of (3aS,7aR)-2-oxo-4,4,7a-trimethyloctahydrobenzofuran (14) [(3aS,7aR)-(−)-compound (14)]

In the same way as in the preparation of the (3aR,7aS)-(+)-compound (14), (3aS,7aR)-(−)-compound (14) (1.10 g, yield 91%) was prepared from the (3aS,7aR)-(−)-compound (13) (1.20 g). Recrystallization from n-hexane gave the (3aS,7aR)-(−)-compound (14) in an amount of 0.960 g.

Melting point: 80°–81° C.

$[\alpha]_D^{24}$: −66.1° (c=0.97, CHCl$_3$).

Elemental analysis: Found: C, 72.74; H, 9.90. Calcd (for C$_{11}$H$_{18}$O$_2$): C, 72.49; H, 9.95.

The IR and NMR spectra of the (3aS,7aR)-compound (14) were the same as those of the (3aR,7aS)-compound (14).

(i) Synthesis of (3aS,7aR)-2-oxo-3-phenylselenyl-4,4,7a-trimethyloctahydrobenzofuran [(3aS,7aR)-(−)-compound]

In the same way as in the preparation of the corresponding (3aR,7aS)-2-oxo-3-phenylselenyl-4,4,7a-trimethyloctahydrobenzofuran compound, the corresponding (3aS,7aR)-phenylselenyl compound (0.60 g, yield 87%) was obtained from the corresponding (3aS,7aR)-compound (14) (0.40 g). The IR and NMR spectra of the resulting compound agreed with those of the corresponding (3aR,7aS)-phenylselenyl compound already reported.

Without purification, this compound was used in the following reaction.

(i) Synthesis of (R)-(−)-oxo-4,4,7a-trimethyl-2,3,5,6,6,7a-hexahydrobenzofuran (15) [(31)-dihydroactinidiolide (15)]

In the same way as in the preparation of the corresponding (S)-(+)-compound (1), the corresponding (R)-(−)-compound (15) (0.23 g, yield 64% from the (3aS,7aR)-compound (14)) was obtained from the corresponding (3aS,7aR)-phenylselenyl compound (0.55 g). Recrystallization from n-hexane gave (R)-(−)-compound (15) (0.19 g).

Melting point: 70°–71° C.

$[\alpha]_D^{24}$: −121.0° (c=1.05, CHCl$_3$).

Elemental analysis: Found: C, 73.39; H, 8.93. Calcd (for C$_{11}$H$_{16}$O$_2$): C, 73.30; H, 8.95.

The IR and NMR spectra of the resulting compound agreed with those of (S)-(+)-compound.

(k) Measurement of the optical purities of the (S)-(+)-compound (15) and (R)-(−)-compound (15)

The optical purities of the (S)-(+)-compound and (R)-(−)-compound were measured by proton NMR (400 MHz) in the presence of a chiral solvation reagent. 10 mg of the (S)-(+)-compound (15) and 46 mg of (−)-2,2,2-trifluoro-1-(9-anthryl)ethanol were dissolved in CDCl$_3$ (0.3 ml). δ (s, vinylic H) 5.31. 10 mg of the (R)-(−)-compound and 46 mg of (−)-2,2,2-trifluoro-1-(9-anthryl)ethanol were dissolved in CDCl$_3$ (0.3 ml). δ (s, vinylic H) 5.36.

Accordingly, both the (S)-(+)-compound (15) and the (R)-(−)-compound (15) had an optical purity of 100% ee.

While the invention has been described in detail and with reference to specific embodiments thereof, it will be apparent to one skilled in the art that various changes and modifications can be made therein without departing from the spirit and scope thereof.

What is claimed is:

1. An optically active hydroxyiodolactone represented by the formula

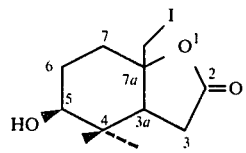
wherein the stereochemistry of the 3a-, 5- and 7a- positions is either (3aR,5S,7aS) or (3aS,5S,7aR).
2. An optically active hydroxyiodolactone as in claim 1, wherein the stereochemistry of the 3a-, 5- and 7a- positions is (3aR, 5 S,7aS).
3. An optically active hydroxyiodolactone as in claim 1, wherein the stereochemistry of the 3a-, 5-, and 7a- positions is (3aS, 5S and 7aR).
* * * * *